United States Patent
Takulapalli et al.

(10) Patent No.: US 7,994,593 B2
(45) Date of Patent: Aug. 9, 2011

(54) QUANTUM WIRE SENSOR AND METHODS OF FORMING AND USING SAME

(75) Inventors: Bharath R. Takulapalli, Tempe, AZ (US); Gerard Laws, Tempe, AZ (US); John Devens Gust, Jr., Mesa, AZ (US); Trevor Thornton, Fountain Hills, AZ (US)

(73) Assignee: The Arizona Board of Regents, Scottsdale, AZ (US)

( * ) Notice: Subject to any disclaimer, the term of this patent is extended or adjusted under 35 U.S.C. 154(b) by 373 days.

(21) Appl. No.: 12/135,940

(22) Filed: Jun. 9, 2008

(65) Prior Publication Data

US 2009/0014757 A1 Jan. 15, 2009

Related U.S. Application Data

(60) Provisional application No. 60/942,954, filed on Jun. 8, 2007.

(51) Int. Cl.
*H01L 27/14* (2006.01)
(52) U.S. Cl. ........... 257/414; 257/E31.086; 438/17; 977/762; 977/936; 977/938; 977/953; 977/957; 977/958
(58) Field of Classification Search ............ 257/414, 257/E31.086; 438/17; 977/762, 936, 938, 977/953, 957, 958
See application file for complete search history.

(56) References Cited

U.S. PATENT DOCUMENTS

| 5,431,883 | A | 7/1995 | Barraud |
| 6,433,356 | B1 | 8/2002 | Cahen et al. |
| 2002/0117659 | A1* | 8/2002 | Lieber et al. ............ 257/14 |
| 2003/0231531 | A1 | 12/2003 | Baxter |
| 2004/0079636 | A1 | 4/2004 | Hsia et al. |
| 2004/0238379 | A1 | 12/2004 | Lindsay et al. |
| 2006/0267051 | A1 | 11/2006 | Gstrein et al. |

FOREIGN PATENT DOCUMENTS

| GB | 2 389 424 B | 11/2004 |
| GB | 2 416 210 A | 1/2006 |

OTHER PUBLICATIONS

Yang, Jinman et al., Molecular Control of the Drain Current in a Buried Channel MOSFET.
Langmuir-Blodgett deposition of Porphyrin molecules for sensing applications.
Bouvet, Marcel, Phthalocyanine-based field-effect transistors as gas sensors, Anal. Bioanal. Chem. (2006) 384: 366-373.
Yang, Jinman et al., Molecular control of the threshold voltage of an NMOS inversion layer, Microelectronic Engineering 63 (2002) 135-139.

(Continued)

*Primary Examiner* — Asok K Sarkar
(74) *Attorney, Agent, or Firm* — Snell & Wilmer L.L.P.

(57) ABSTRACT

A solid-state field-effect transistor device for detecting chemical and biological species and for detecting changes in radiation is disclosed. The device includes a quantum wire channel section to improve device sensitivity. The device is operated in a fully depleted mode such that a sensed biological, chemical or radiation change causes an exponential change in channel conductance of the transistor.

20 Claims, 14 Drawing Sheets

OTHER PUBLICATIONS

Laws, G. M., Drain current control in a hybrid molecular/MOSFET device, Physica E 17 (2003) 659-663.

Yang, Jinman et al., Controlling the threshold voltage of a metal-oxide-semiconductor field effect transistor by molecular protonation of the Si:SiO2 interface, J. Vac. Sci. Technol. B 20(4), Jul./Aug. 2002.

Takulapalli, Bharath, Molecular Sensing Using Monolayer Gate Fully Depleted Silicon on Insulator Nano MOSFETS, Aug. 2006.

Shepherd L. et al., Weak Inversion ISFETs for ultra-low power biochemical sensing and real-time analysis, Sensors and Actuators B, Elsevier Sequoia S.A., Lausanne, CH, vol. 107, No. 1, May 27, 2005, pp. 468-473. ISSN: 0925-4005.

Martinoia S. et al., A behavioral macromodel of the ISFET in SPICE, Sensors and Actuators B, Elsevier Sequoia S. A., Lausanne, CH, vol. 62, No. 3, Mar. 1, 2000, pp. 182-189. ISSN: 0925-4005.

Takulapalli Bharath, Detection of Pyridine using ZnTCPP SAM Coated SOI Mosfet Devices, Jun. 9, 2006.

Ashcroft, B., et al. Calibration of a PH Sensitive Buried Channel Silicon-on-Insulator MOSFET for Sensor Applications Jul. 28, 2004.

* cited by examiner

QUANTUM WIRE SENSOR AND METHODS OF FORMING AND USING SAME

CROSS-REFERENCE TO RELATED APPLICATIONS

This application claims the benefit of provisional application No. 60/942,954, entitled FULLY DEPLETED EXPONENTIALLY COUPLED (FDEC) NANOWIRE/QUANTUM WIRE SENSOR, filed Jun. 8, 2007, the contents of which are hereby incorporated herein by reference.

GOVERNMENT LICENSE RIGHTS

The U.S. Government has a paid-up license in this invention and the right in limited circumstances to require the patent owner to license others on reasonable terms as provided for by the terms of Grant No. ECS-0097434 awarded by The National Science Foundation.

FIELD OF INVENTION

The invention generally relates to solid-state sensors. More particularly, the invention relates to quantum wire field effect transistor sensors and to methods of making and using the sensors.

BACKGROUND OF THE INVENTION

Solid-state sensors may be used in a wide variety of applications. For example, chemical solid-state sensors may be used for real-time analysis of chemical mixtures in both continuous and discrete sampling modes. Similarly, biological sensors can be used to detect biological agents and hazards and radiation sensors can be used to detect types and amounts of radiation.

The sensors may be used to detect a single component in a complex mixture, such as a toxic molecule in ambient atmosphere, analyze multiple components in a composition, or perform characterization and quality assessment of complex mixtures—e.g., as used to characterize odors, tastes, smells, etc., by pattern recognition methods using array-based sensors.

Typical solid-state sensors generally include a detection or receptor element and signal transduction means. The receptor layer interacts with the target specie(s)—e.g., by physical absorption or physisorption, chemisorption, microencapsulation, or the like. The transducer converts a change at the receptor surface into a measurable electrical signal. The signal transduction, or coupling of signal between the receptor and the transducer may be linear, nonlinear, logarithmic or exponential in relation. The coupling relation between the two elements generally determines the sensitivity of the device.

A variety of signal transducer elements, such as potentiometric sensors, amperometric sensors, conductometric sensors, field effect transistor (FET) based sensors, optical sensors, thermal sensors, gravimetric or piezo-electric sensors, and the like, have been developed. FET devices may be particularly desirable because the FET devices exhibit relatively fast and sensitive signal transduction, are relatively easy to use, and are relatively easy to integrate with other sensor components.

In the case of FET devices, the metal gate of the field effect transistor device is either replaced or coated with a sensitive thin film, insulator or membrane, which acts as the signal detection element. The FET devices work on the general principal of detecting shifts in localized electric potential due to interactions at the device surface. The FET device transduces a detection event into an electrical signal by way of change in the conductance of the channel region leading to a change in the drain current. The FET device may be operated as a sensor either by biasing the device with constant gate voltage and measuring the change in the current or by detecting the change in gate voltage required to maintain a constant current.

Metal-Oxide-Semiconductor FET (MOSFET) type sensors are often operated in inversion mode, where inversion current is established in the semiconductor channel by biasing the metal gate of the MOSFET. In these devices, target molecule binding at the sensitive thin film or a change in radiation level modulates the minority charge carrier density in the inversion channel. Hence, inversion current in a bulk p-type MOSFET decreases upon addition of negative charge to the device surface.

Although such devices and transducer elements have been shown to work for some sensing applications, the non-FET devices are relatively bulky and expensive, and the FET-based devices may be relatively unstable and exhibit relatively low sensitivity. Accordingly, improved sensors and methods of making and using sensors are desired.

SUMMARY OF THE INVENTION

The present invention provides a highly sensitive sensor suitable for detecting chemical, biological, and/or radioactive species. While the ways in which the present invention addresses the various drawbacks of the prior art are discussed in greater detail below, in general, the invention provides a field-effect transistor (FET) having a quantum-wire channel to improve device sensitivity.

In accordance with various embodiments of the invention, a sensor includes a substrate, an insulator formed overlying the substrate, and a quantum wire channel formed overlying the insulator. In accordance with various aspects of these embodiments, a top surface of the channel layer acts as a receptor or sensitive layer that interacts with chemical, biological, or radioactive species. In accordance with alternative aspects, the sensor further includes a sensitive layer overlying the quantum wire channel.

In accordance with additional embodiments of the invention, the sensor further includes a dielectric layer overlying the channel. In accordance with some aspects of the exemplary embodiments, the dielectric layer acts as a receptor or sensitive layer that interacts with chemical, biological, and/or radioactive species.

In accordance with yet further embodiments, the sensor includes a sensitive layer formed overlying the dielectric layer.

In accordance with various additional aspects, a quantum wire thickness ranges from about 1 Angstrom to about 1000 nm.

In accordance with further various aspects, the sensor is configured to operate in a fully depleted mode, such that a negative charge added to the quantum wire layer, sensitive layer or the dielectric layer causes an increase in electron inversion channel conductance for n-channel FET devices and addition of positive charge to the n-channel FET decreases the inversion channel conductance, while an addition of a negative charge to the quantum wire layer, sensitive layer or the dielectric layer of a p-channel device causes a decrease in electron inversion channel conductance and addition of positive charge to the surface increases the inversion channel conductance.

In accordance with yet further embodiments, the sensor includes an additional layer between the quantum wire and the dielectric layer.

In accordance with further embodiments, a sensor includes additional material to form a heterostructure with the quantum wire layer. The additional material may be in the form of one or more layers or discrete islands of one or more layers of material.

In accordance with various additional embodiments of the invention, the sensor is a biological sensor.

In accordance with yet additional embodiments, the sensor is a chemical sensor.

In accordance with yet further embodiments, the sensor is a radiation sensor.

In accordance with additional embodiments of the invention, a method of forming a sensor includes providing a substrate (e.g., a p-type SOI silicon wafer), thinning a channel region (e.g., using a wet oxidation followed by a seed layer of dry oxide), forming a doping mask over a portion of the substrate or wafer (e.g., by etching a portion of the oxide layer formed using the wet oxidation followed by a seed layer of dry oxide step), forming a doped region within the channel region, forming a mask for source and drain regions, forming the source and drain regions, removing any excess masking materials, optionally forming device isolation regions (e.g., using photoresist patterning and plasma etching), patterning and removing a portion of the active region to form one or more quantum wires, and forming contacts. In accordance with various aspects of these embodiments, quantum wires or nanowires are formed by patterning the channel region (e.g., using electron beam lithography) and etching (e.g., using SF6 in an REI apparatus) the region to form the quantum wires.

In accordance with further aspects of these embodiments, a chemical, biological, and/or radiation sensitive material is formed overlying the quantum wire channel. In accordance with yet further aspects, a dielectric layer is formed overlying channel region. In accordance with yet further aspects, a sensitive layer is formed overlying the dielectric layer. And, in accordance with yet additional aspects of the invention, one or more additional material layers may be included in the sensor structure.

In accordance with alternative embodiments of the invention, a local oxidation of silicon (LOCOS) process is used to achieve device isolation. In accordance with various aspects of these embodiments, the method includes providing an SOI wafer, selectively etching silicon in the channel region of the device to a predetermined depth (e.g., using a reactive ion etch), forming quantum or nanowire structures in the channel region, forming a diffusion mask layer, forming a field oxide (e.g., using a wet oxidation process) to consume silicon in the channel region, doping a portion of the device, and forming substrate contacts. In accordance with further aspects of these embodiments, a chemical, biological, and or radiation sensitive material is formed overlying the channel region. In accordance with yet further aspects, a dielectric layer is formed overlying the channel region. In accordance with yet further aspects, a sensitive layer is formed overlying the dielectric layer. And, in accordance with yet additional aspects of the invention, one or more additional material layers may be included in the sensor structure.

In accordance with yet further embodiments, the sensor is formed using flexible substrate technology.

In accordance with yet further embodiments of the invention, a chemical, biological, or radioactive species is sensed using a fully-depleted exponentially-coupled quantum-wire sensor.

Elements in the figures are illustrated for simplicity and clarity and have not necessarily been drawn to scale. The dimensions of some of the elements in the figures may be exaggerated relative to other elements to help to improve understanding of embodiments of the present invention.

DETAILED DESCRIPTION

The present invention provides an improved solid-state sensor for detection of biological and chemical species and for radiation detection. More particularly, the invention provides a field-effect transistor (FET) including quantum wire(s) or nanowire(s), which operates as a fully-depleted exponentially-coupled (FDEC) sensor. As discussed in greater detail below, a threshold voltage or channel conductance of the sensor is manipulated as sensed biological, chemical, or radioactive species are detected, causing an exponential change in channel current.

The exponential change of channel current of the sensors of the present invention is in an opposite direction compared to that of typical FET sensors, and increases in n-channel type devices upon detection of species having excess electron charge or negative charge. Such an exponential response makes the sensors of the present invention more sensitive for qualitative and quantitative analysis.

Figure 1:
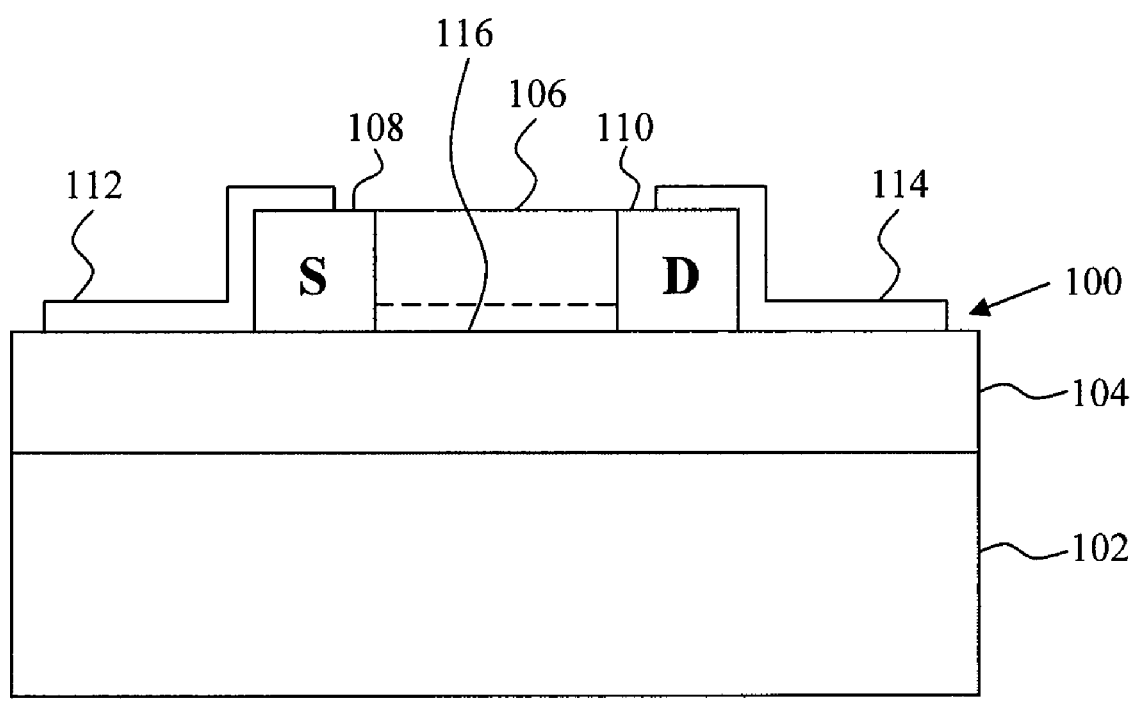
FIG. 1 illustrates a sensor in accordance with various embodiments of the present invention.

FIG. 1 illustrates a sensor 100 in accordance with various embodiments of the invention. Sensor 100 includes a base or substrate 102, an insulator layer 104, a nanowire or quantum wire channel region 106, a source 108, a drain 110, and contacts 112, 114. It should be noted that quantum wire and nanowire are used interchangeably and the terms are meant to describe a structure having a dimension less than about 1000 nm, as discussed in more detail below.

In operation, sensor 100 is operated in inversion mode, where an inversion current is established in channel region 106 by biasing gate or base 102. As target molecules bind to a surface of sensor 100, the inversion threshold voltage is thought to be modulated by a second-order capacitive charge coupling mechanism involving interface defect states, resulting in an exponential increase in device response. This unique exponential coupling of the device response to the surface charge imparted by the target species on the sensor surface leads to the fully-depleted exponentially-coupled (FDEC) sensor.

In contrast to the present invention, the prior art teaches inversion-based FET devices applied for chemical sensing, with variations of device structure in a manner where addition of negative charge to the surface of an n-channel FET causes a decrease in inversion channel conductance (or drain current decrease), and addition of positive charge causes an increase in inversion channel conductance; and where, in a p-channel FET, addition of negative charge to the surface of the device causes an increase in channel conductance (or drain current increase) and addition of positive charge causes a decrease in channel conductance. Such response of device structures is in opposite direction to the device of the present invention in this application. As noted above, in accordance with various embodiments of the invention, the addition of negative charge to the surface of an n-channel inversion based FET device in accordance with the present invention increases the inversion channel conductance, and addition of positive charge to the surface decreases the inversion channel conductance, while addition of negative charge to the surface of a p-channel inversion based device decreases the inversion channel conductance and addition of positive charge to the surface increases the inversion channel conductance.

Referring again to FIG. 1, base 102 acts as a gate during sensor 100 operation. Base 102 may be formed of any suitable material. Examples include, but are not limited to metals and metal nitrides such as Ge, Mg, Al, Sc, Ti, V, Cr, Mn, Fe, Co, Ni, Cu, Zn, Ga, Y, Zr, Nb, Mo, Ru, Rh, Pd, Ag, La, Hf, Ta, W, Re, Os, Ir, Pt, Au, TaTi, Ru, HfN, TiN, and the like, metal alloys, semiconductors, such as Group IV (e.g., silicon) Group III-IV (e.g., gallium arsenide) and Group II-VI (e.g., cadmium selenide), metal-semiconductor alloys, semi metals, or any organic or inorganic material that acts as a MOSFET gate.

A thickness of basic 102 may vary according to material and application. In accordance with one example, base 102 is substrate silicon in silicon-on-insulator (SOI) wafer.

In another example, base 102 is a flexible substrate, for example, an organic material, such as pentacene.

Insulator layer 104 acts as a gate insulator or gate dielectric during operation of sensor 100. Layer 104 may be formed of any suitable material, such as any suitable organic or inorganic insulating material. Examples include, but are not limited to, silicon dioxide, silicon nitride, hafnium oxide, alumina, magnesium oxide, zirconium oxide, zirconium silicate, calcium oxide, tantalum oxide, lanthanum oxide, titanium oxide, yttrium oxide, titanium nitride, and the like. One exemplary material suitable for layer 104 is a buried oxide layer in an SOI wafer. A thickness of layer 104 may also vary according to material and application. By way of one particular example, layer 104 is silicon oxide having a thickness from about 1 nm to 100 microns; in accordance with other aspects, layer 104 may be 1 mm or more.

Channel region 106 includes quantum wires or nanowires, which may be formed of a variety of materials, such as crystalline or amorphous inorganic semiconductor material, such as those used in typical MOS technologies. Examples include, but are not limited to, elemental semiconductors, such as silicon, germanium, diamond, tin; compound semiconductors, such as silicon carbide, silicon germanium, diamond, graphite; binary materials, such as aluminium antimonide (AlSb), aluminium arsenide (AlAs), aluminium nitride (AlN), aluminium phosphide (AlP), boron nitride (BN), boron phosphide (BP), boron arsenide (BAs), gallium antimonide (GaSb), gallium arsenide (GaAs), gallium nitride (GaN), gallium phosphide (GaP), indium antimonide (InSb), indium arsenide (InAs), indium nitride (InN), indium phosphide (InP), cadmium selenide (CdSe), cadmium sulfide (CdS), cadmium telluride (CdTe), zinc oxide (ZnO), zinc selenide (ZnSe), zinc sulfide (ZnS), zinc telluride (ZnTe), cuprous chloride (CuCl), lead selenide (PbSe), lead sulfide (PbS), lead telluride (PbTe), tin sulfide (SnS), tin telluride (SnTe), bismuth telluride ($Bi_2Te_3$), cadmium phosphide ($Cd_3P_2$), cadmium arsenide ($Cd_3As_2$), cadmium antimonide ($Cd_3Sb_2$), zinc phosphide ($Zn_3P2$), zinc arsenide ($Zn_3As_2$), zinc antimonide ($Zn_3Sb_2$), other binary materials such as lead(II) iodide ($PbI_2$), molybdenum disulfide ($MOS_2$), gallium selenide (GaSe), tin sulfide (SnS), bismuth sulfide ($Bi_2S_3$), platinum silicide (PtSi), bismuth(III) iodide ($BiI_3$), mercury(II) iodide ($HgI_2$), thallium(I) bromide (TlBr), semiconducting oxides like zinc oxide, titanium dioxide ($TiO_2$), copper(I) oxide ($Cu_2O$), copper(II) oxide (CuO), uranium dioxide ($UO_2$), uranium trioxide ($UO_3$), 6.1 Å materials or ternary materials, such as aluminium gallium arsenide (AlGaAs, AlxGal-xAs), indium gallium arsenide (InGaAs, InxGal-xAs), aluminium indium arsenide (AlInAs), aluminium indium antimonide (AlInSb), gallium arsenide nitride (GaAsN), gallium arsenide phosphide (GaAsP), aluminium gallium nitride (AlGaN), aluminium gallium phosphide (AlGaP), indium gallium nitride (InGaN), indium arsenide antimonide (InAsSb), indium gallium antimonide (InGaSb), cadmium zinc telluride (CdZnTe, CZT), mercury cadmium telluride (HgCdTe), mercury zinc telluride (HgZnTe), mercury zinc selenide (HgZnSe), lead tin telluride (PbSnTe), thallium tin telluride ($Tl_2SnTe_5$), thallium germanium telluride ($Tl_2GeTe_5$) and quaternary materials, such as aluminum gallium indium phosphide (AlGaInP, IAlGaP, InGaAlP, AlInGaP), aluminum gallium arsenide phosphide (AlGaAsP), indium gallium arsenide phosphide (InGaAsP), aluminium indium arsenide phosphide (AlInAsP), aluminum gallium arsenide nitride (AlGaAsN), indium gallium arsenide nitride (InGaAsN), indium aluminum arsenide nitride (InAlAsN), copper indium gallium selenide (CIGS), or quinary materials like gallium indium nitride arsenide antimonide (GaInNAsSb), and the like.

Channel region 106 can also be made of organic semiconducting materials. Examples of such materials include, but are not limited to, polyacetylene, polypyrrole, polyaniline, Rubrene, phthalocyanine, poly(3-hexylthiophene, poly(3-alkylthiophene), α-ω-hexathiophene, Pentacene, α-ω-dihexyl-hexathiophene, α-ω-dihexyl-hexathiophene, poly(3-hexylthiophene), bis(dithienothiophene, α-ω-dihexyl-quaterthiophene, dihexyl-anthradithiophene, n-decapentafluoroheptylmethylnaphthalene-1,4,5,8-tetra-carboxylic diimide, α-ω-dihexyl-quinquethiophene, N,N'-dioctyl-3,4,9,10-perylene tetracarbozylic , CuPc, methanofullerene, [6,6]-phenyl-C61-butyric acid methyl ester (PCBM), C60, 3',4'-dibutyl-5-5bis(dicyanomethylene)-5,5'-dihydro-2,2':5',2"terthiophene (DCMT), PTCDI-C5, P3HT, Poly(3,3"-dialkyl-terthiophene), C60-fused N-methylpyrrolidine-meta-C 12 phenyl (C60MC 12), Thieno[2,3-b] thiophene, PVT, QM3T, DFH-nT, DFHCO-4TCO, BBB, FTTTTF, PPy, DPI-CN, NTCDI, F8T2-poly[9,9' dioctylfluorene-co-bithiophene], MDMO-PPV-poly[2-methoxy-5-(3,7-dimethyloctyloxy)]-1,4-phenylenevinylene, P3HT-regio-regular poly[3-hexylthiophene]; PTAA, polytriarylamine, PVT-poly-[2,5-thienylene vinylene], DH-5T-α,ω-Dihexylquinquethiophene, DH-6T-α,ω-dihexylsexithiophene, phthalocyanine, α-6T-α-sexithiophene, NDI, naphthalenediimide, F16CuPc-perfluorocopperphthalocyanine, perylene, PTCDA-3,4,9,10-perylene-tetracarboxylic dianhydrid and its derivatives, PDI-N,N'-dimethyl 3,4,9,10-perylene tetra-carboxylicdiimide, or the like.

During operation of sensor 100, an inversion channel 116 is formed at the channel region 106/insulator layer 104 interface by controlling a voltage bias at base 102. Alternatively an inversion channel 116 may be formed in channel region 106 with no bias on base 102, depending of channel region 106 doping, thickness of region 106, and other such variables, and the fixed oxide charge density and interface trap states density at channel 106 boundaries. A thickness of channel region 106 can be from about 1 nm about to about 10 microns, depending on the material and its doping density.

When biasing base 102 to obtain an inversion channel in channel region 106, the thickness (t) of channel region 106 should be such that the whole thickness of channel region 106 should be fully depleted before the formation of inversion channel at channel region 106—insulator 104 interface, as illustrated in the following formula.

$$\text{thickness}(t) < \text{depletion} - \text{width}(w) \sim \sqrt{\frac{4k\varepsilon_0 \Phi_F}{qN_{A/B}}}$$

Where,
k is the relative dielectric constant of semiconductor
$\varepsilon_o$ is the permittivity of free space
q is the electron charge
$N_{A/B}$ is the concentration of donors/acceptors
$\Phi_F$ is the potential difference between Fermi level and intrinsic level in the semiconductor The above equation defines a thickness (t) of channel region 106, in one case, as suitable in device of one example of the present invention, and is less than the full depletion width (w) of the given semiconductor material.

For example, in the case of channel region 106 being a silicon thin film, if the doping density is 1 E 17, a thickness of the channel region 106 should be less than about 200 nm. Whereas, if the doping density is 1 E 14, the thickness of the layer is less than about 4 microns. Stated another way, a thickness of inversion layer 116 is less than the depletion layer width for the given doping density in channel region 106.

Channel region 106 may be doped p-type or n-type, corresponding to n-channel devices and p-channel devices, respectively. The above equation corresponds to a case of a channel region 106 with no extra delta doping profile or similar other extra steps used to modulate the conductance of the channel region, inversion threshold, or the like. In case of use of delta doping or the like in channel region 106, the analysis and the thickness of channel region 106 will vary accordingly.

One exemplary channel region 106 includes 1 E 15 doped p-type silicon layer of thickness about 100 nm. An inversion layer is formed in this silicon thin film at the silicon-buried oxide interface by biasing base 102.

In accordance with various embodiments of the invention, the nanowire width ranges from about 1 Angstrom to about 1000 nm.

Source and drain doped regions 108, 110 are formed on either side of the channel region 106 using known doping techniques. In accordance with one example, source and drain regions are 1 E 19 phosphorous doped N++ regions formed in a p-type silicon.

Figure 2:
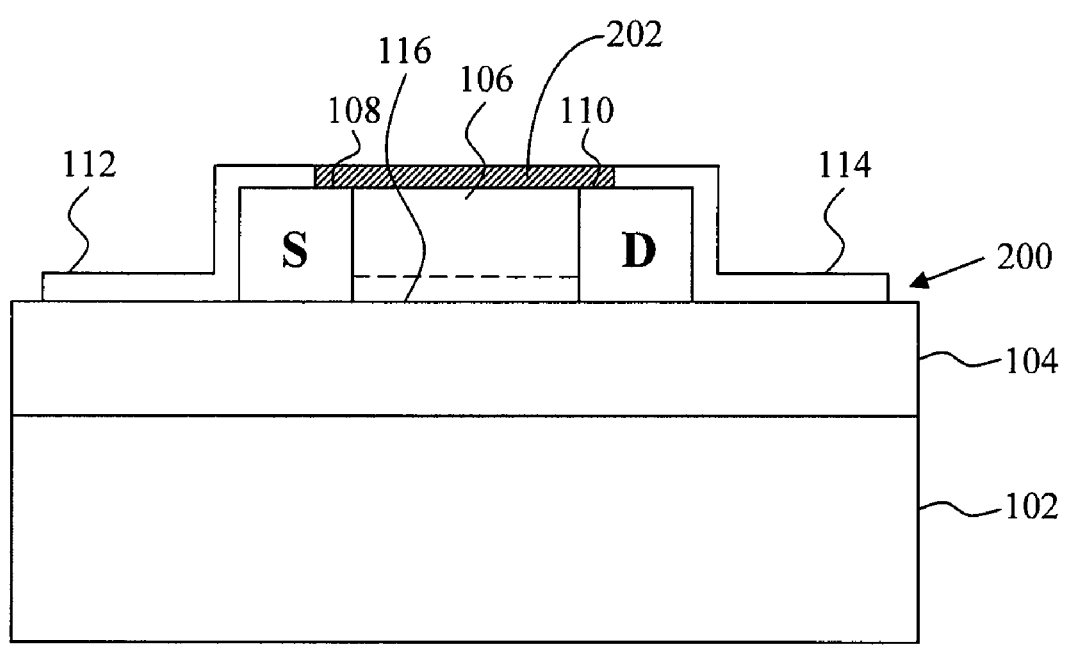
FIG. 2 illustrates a sensor in accordance with additional embodiments of the invention.

FIG. 2 illustrates another sensor 200 in accordance with additional exemplary embodiments of the invention. Sensor 200 is similar to sensor 100, except sensor 200 includes an additional dielectric layer 202. Exemplary materials suitable for dielectric layer 202 include inorganic dielectric material that acts as a gate dielectric material. Examples include, but are not limited to, $SiO_2$, $Si_3N_4$, SiNx, $Al_2O_3$, AlOx $La_2O_3$, $Y_2O_3$, $ZrO_2$, $Ta_2O_5$, $HfO_2$, $HfSiO_4$, HfOx, $TiO_2$, TiOx, a-$LaAlO_3$, $SrTiO_3$, $Ta_2O_5$, $ZrSiO_4$, BaO, CaO, MgO, SrO, $BaTiO_3$, $Sc_2O_3$, $Pr_2O_3$, $Gd_2O_3$, $Lu_2O_3$, TiN, $CeO_2$, BZT, BST, or a stacked or a mixed composition of these and/or such other gate dielectric material(s).

Dielectric layer 202 can additionally or alternatively include an organic gate dielectric material. Examples of organic materials include, but are not limited to, PVP-poly (4-vinyl phenol), PS-polystyrene, PMMA-polymethyl-methacrylate, PVA-polyvinyl alcohol, PVC-polyvinylchloride, PVDF-polyvinylidenfluoride, PαMS-poly[α-methylstyrene], CYEPL-cyano-ethylpullulan, BCB-divinyltetramethyldisiloxane-bis(benzocyclobutene), CPVP-Cn, CPS-Cn, PVP-CL, PVP-CP, polynorb, GR, nano $TiO_2$, OTS, Pho-OTS, various self-assembled monolayers or multilayers or a stacked or a mixed composition of these and such other organic gate dielectric material.

Dielectric layer 202 can also be of material that is an intrinsic or lowly doped semiconducting material, with low density of charge carriers and low carrier mobility, which is semi-insulating in nature.

In accordance with exemplary aspects of various embodiments of the invention, the processing and fabrication of dielectric layer 202 is done in a controlled fashion, such that the interface state density levels and other such defect states at the layer 202—channel region 106 interface are "optimized." For example, use of Si [111]-SiO2 interface produces larger interface state density compared to Si [100]-SiO2 interface. Optimization of traps does not necessarily mean maximization of interface state density levels, but means application-specific control of interface state densities at that interface in order to manipulate or maximize the resulting sensor signal. In one case, the dielectric layer 202 material is chosen to be a material that acts as both dielectric layer and chemical sensitive layer at the same time. An example of this is use of yttrium oxide ($Y_2O_3$) as the gate dielectric, which can be used to sense sulfur mustard gas, since $Y_2O_3$ reacts with mustard gas.

A thickness of layer 202 may vary from application to application and is typically between about 2 Angstroms and 100 mn.

Figure 3:
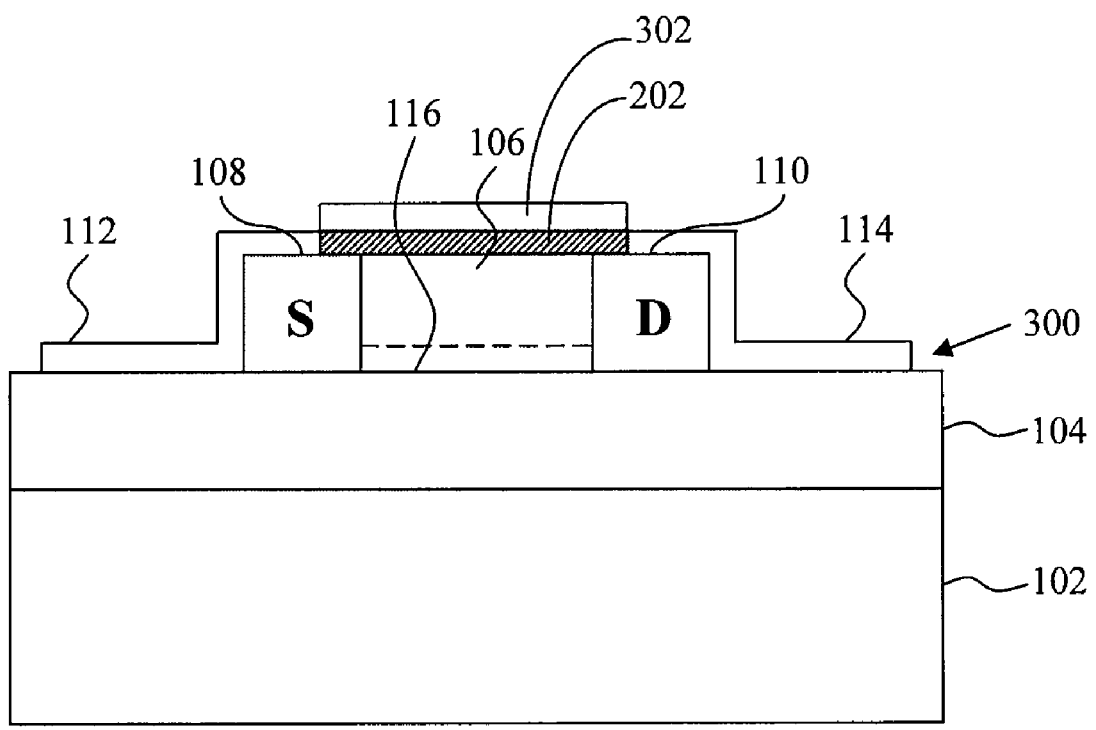
FIG. 3 illustrates a sensor in accordance with yet further embodiments of the invention.

FIG. 3 illustrates another sensor 300 in accordance with additional embodiments of the invention. Sensor 300 is similar to sensor 200, except sensor 300 includes an additional layer 302, which is sensitive to biological, chemical, and/or radioactive material.

Layer 302 is designed to be sensitive to species in the ambient, in, for example, gas phase or in liquid phase. Layer 302 could also be chosen to be sensitive to radiation, where it is applied as a radiation sensitive device.

Layer 302 can be organic or inorganic or conducting or insulating or semiconducting or metallic in nature and can include any suitable material. A thickness of layer 302 can be generally from about 1 Angstrom to about 1000 nanometers. One exemplary material for layer 302 is zinc porphyrin molecular monolayer that can been used to detect an amine molecule-piperidine.

Layer 302 can be in the form of a continuous layer, particles of various sizes, discrete islands of material, a semi-continuous layer, a stack of layers of different materials, combinations of these structures, and the like, which act to interact selectively with various biological, chemical, and radioactive species. In accordance with additional embodiments of the invention, further layers, that may be continuous, semi-continuous, discrete islands, or particles, can be added above layer 302 in order to increase the capacitive coupling of charge with the interface trap density at the channel region 106—dielectric layer 202 interface, and, in turn, inversion layer 116 formed in channel region 106.

Particular exemplary materials suitable for layer 302 include:

Antibody: antigen binding specific organic or inorganic molecules or biomolecules can be detected with high sensitivity and selectivity using a device coated with antibody(s) or antigen(s) biomolecules. For example, a sensor including a biotin layer can be used to detect Avidin and Streptavidin molecules.

DNA hybridization sensor: an array of single stranded DNA oligomers, of any base pair lengths, can be attached to the surface of the devices, and used as layer 302. In this case, device 300 can be used to detect corresponding complementary DNA strands by way of DNA hybridization over the device surface. Device 300, coated with such an array of DNA strands, single stranded or double stranded depending on application, can be used for target DNA identification or for detection of specific ions or organic molecules, biomolecules, virus or bacteria, or the like. A large array of devices terminated with predetermined arrays of DNA oligomers can be used for DNA sequencing applications.

Nerve agent sensor: a Di-azo group, for example 3,5-dichlorophenyldiazomethane or its phenyl derivative, can be used as layer 302 to detect presence of Methylphosphonic Acid (MPA), which is a product of atmospheric hydrolysis of all nerve agents, and hence can detect presence of nerve agents in the ambient in a selective fashion. Or, layer 302 may include positive ion terminations of Cu++ on organic molecules, and sensor 300 can be used for high sensitivity measurement of nerve agents.

Metallo Porphyrin array sensor: a predetermined, select array of specific organic molecule monolayers and multilayers. For example Metallo porphyrins can also be used as layer 302 to detect a variety of organic vapors in gas or ions in solutions with varying sensitivity and selectivity.

Mustard gas sensor: Layer 302 may include Guanine terminated DNA oligomer to sense sulfur mustard gas. Alternatively, layer 302 may include $Y_2O_3$ nano-crystals, to detect mustard gas.

Molecular Imprinted surface: Layer 302 may include "molecular imprinted" molecules or monolayers or multi layers or thin films or polymer matrices, that bind to a specific predetermined target molecule to realize highly selective sensors. By using an Epitome (a specific portion of a large molecule like protein) based approach, wherein the molecular imprint of the smaller Epitome in a monomer—cross linker matrix is used, larger molecules like proteins, DNA and other biomolecules are detected by selected binding at the Epitome site.

Ion sensor: Layer 302 may include specific organic molecules or inorganic thin films that can be used to sense ions in solution with high selectivity. For example, a thin film (e.g., up to about few monolayers) of urea (N,N"-(9,10-dihydro-9,10-dioxo-1,2-anthracenediyl)bis[N'-phenyl] can be used to detect fluoride ion with high selectivity.

Figure 4:
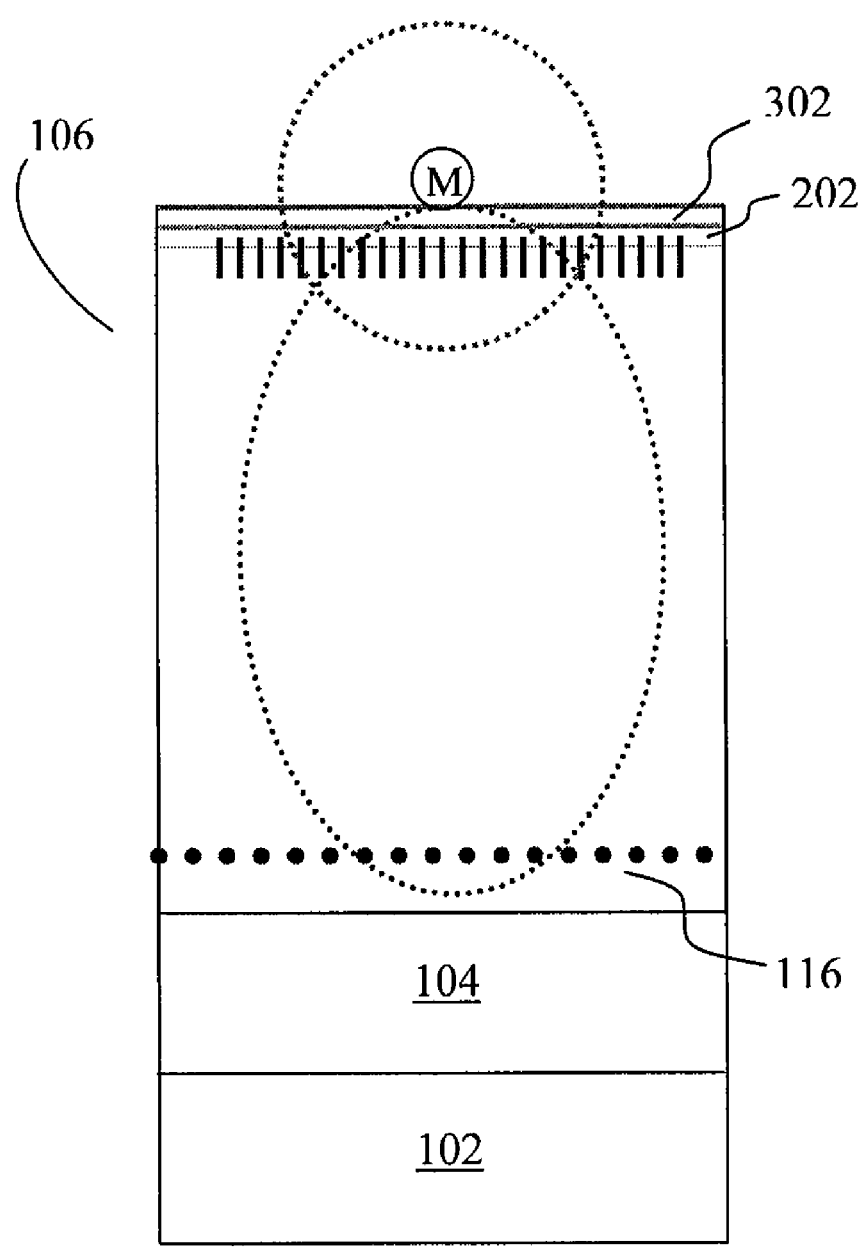
FIGS. 4 and 5 illustrate operation of the sensor illustrated in FIG. 3.
Figure 5:
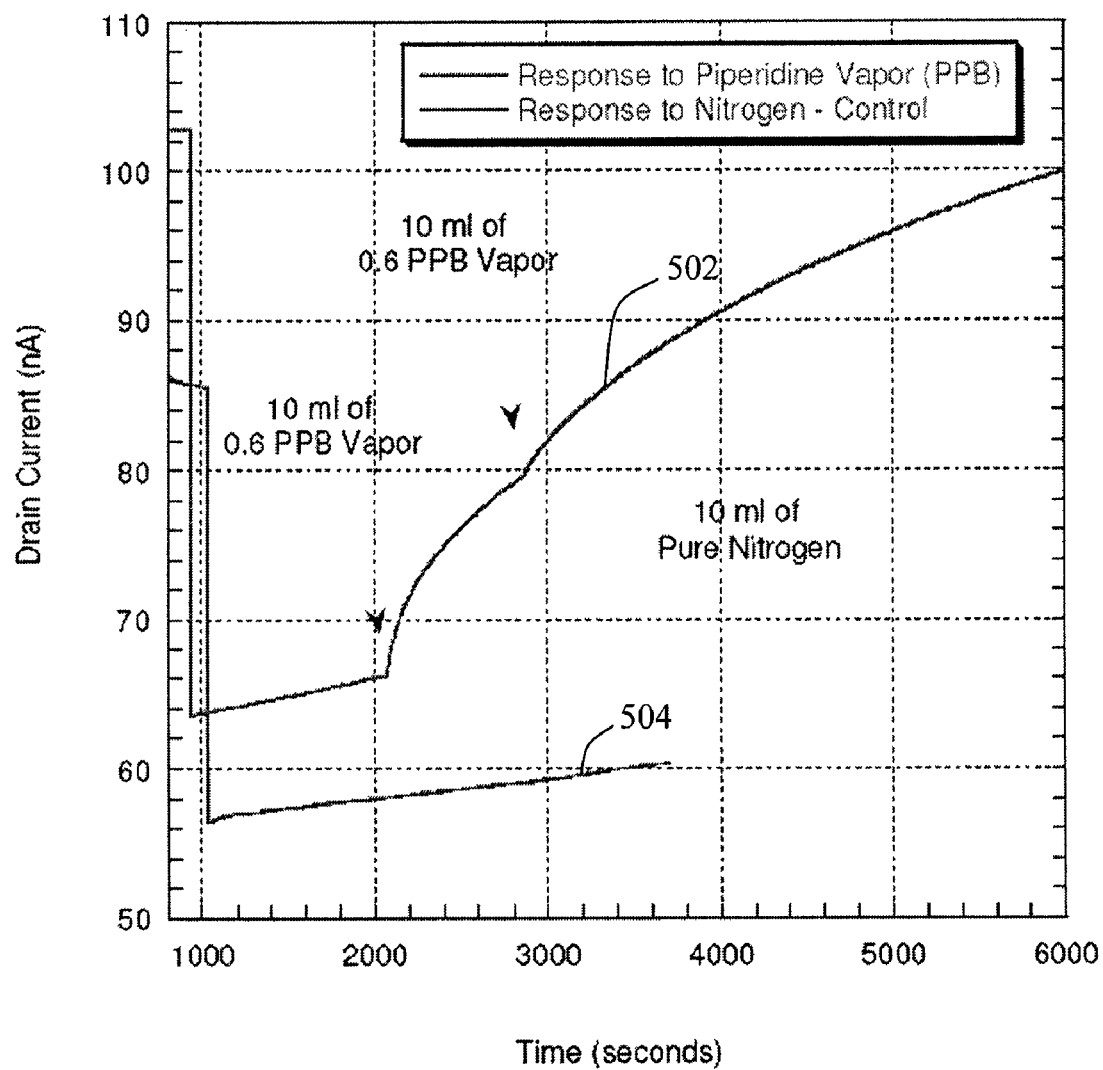

Operation of an exemplary sensor 300 is illustrated in FIGS. 4 and 5. Referring to FIG. 4, upon binding of analyte molecule M at the surface of layer 302, the interface states at channel region 106—dielectric layer 202 interface that come inside the potential field/electric field of influence of target species M, either emit or accept electrons (or holes), depending on the field of M, causing a modulation in occupancy of interface states. Modulation of interface state occupancy at the channel region 106—dielectric layer 202 interface, in-turn, changes the potential of the channel region 106 at the channel region 106—insulator 104 interface, in a fully depleted semiconductor channel region 106, causing a change in the threshold voltage of inversion channel 116 formed in channel region 106 channel at the channel region 106—insulator layer 104 interface. This indirect coupling of the field of species M causes modulation of occupancy of interface traps at channel region 106—dielectric layer 202 interface, which, in turn, changes the threshold voltage of the inversion channel formed in channel region 106. This effect is referred to as the "Fully Depleted Exponentially coupling" (FDEC) effect.

In another exemplary embodiment of the invention, the same inversion channel conductance modulation, as shown in FIG. 4, can be achieved, rather than by modulation of interface state occupancy, by modulation of trapped charges or impurity doping and similar other charge center modulation in insulator dielectric layer 202 or in channel region 106 due to binding of chemical moiety at the surface of the device.

FIG. 5 illustrates a device response, where addition of electron donating species (piperidine molecules) to layer 302 (e.g., zinc porphyrin molecular monolayer), causes an increase in electron charge at the surface of dielectric layer 202 (e.g., a native silicon oxide), which in turn increases the electron inversion channel conductance (or drain current increases) in channel 106 (e.g., silicon) due to decrease in threshold voltage of the electron inversion channel 116. In the illustrated example, an increase in device drain current of a 500 nm device when the n-channel device is exposed to 0.6 PPB of piperidine molecules (line 502), compared to control experiment where just inert gas is introduced (line 504), establishes the device as a highly sensitive sensor.

Referring again to FIGS. 2-3, in accordance with various additional embodiments of the invention, one or more layers can be introduced between channel region 106 and dielectric layer 202. The nature of these layers can be insulating or semi insulating or semi conducting or semi metallic. One example of this is to use a thin layer of germanium, having a thickness of about 1 nm to about 100 nm sandwiched between channel region 106 and dielectric layer 202 or alternately, between channel region 106—dielectric layer 202 interface and insulator 104—channel region 106 interface. The stacking in this example could be Si (channel region 106), Ge (the extra layer) and oxide (dielectric layer 202) or Si (channel region 106), Ge (the extra layer), Si (another extra layer) and oxide (dielectric layer 202). In the same way, a stack of layers of different materials can be used between channel region 106 and dielectric layer 202. These extra layers may be desired to increase the efficiency of the sensor signal or for specific sensor applications. In all these examples of stacked structures, similar to the five layer structure above (illustrated in FIG. 3), the addition of negative charge to the surface of an n-channel inversion based FET device (electrons are the carriers in inversion channel) increases the inversion channel conductance, and addition of positive charge to the surface decreases the inversion channel conductance; while addition of negative charge to the surface of a p-channel inversion based device (holes are the carriers in inversion channel) decreases the inversion channel conductance and addition of positive charge to the surface increases the inversion channel conductance.

Fabrication of Specific Examples:

Fabrication of a device in accordance with one embodiment of the invention is illustrated in FIGS. 6-14. The illustrated process can be used to form device 300, illustrated in FIG. 3 using nanowire or quantum-wire silicon-on-insulator (SOI) inversion mode FET device, where base 102 is substrate silicon of an SOI wafer, insulator 104 is a buried oxide layer of the SOI wafer, channel region 106 is a top nanowire or quantum-wire silicon on insulator layer, dielectric layer 202 is native oxide layer, and sensitive layer 302 is a chemical sensitive layer that binds specific target molecules in ambient, here a zinc porphyrin molecular monolayer. The exemplary process flow is for an n-channel, p-type bulk, silicon on insulator wafer using standard n-MOS process technology. It will be appreciated that fabrication can be done in a variety of ways, depending on the materials chosen for the various device layers, the process technology steps chosen to realize the sensor device, and the like.

Figure 6:
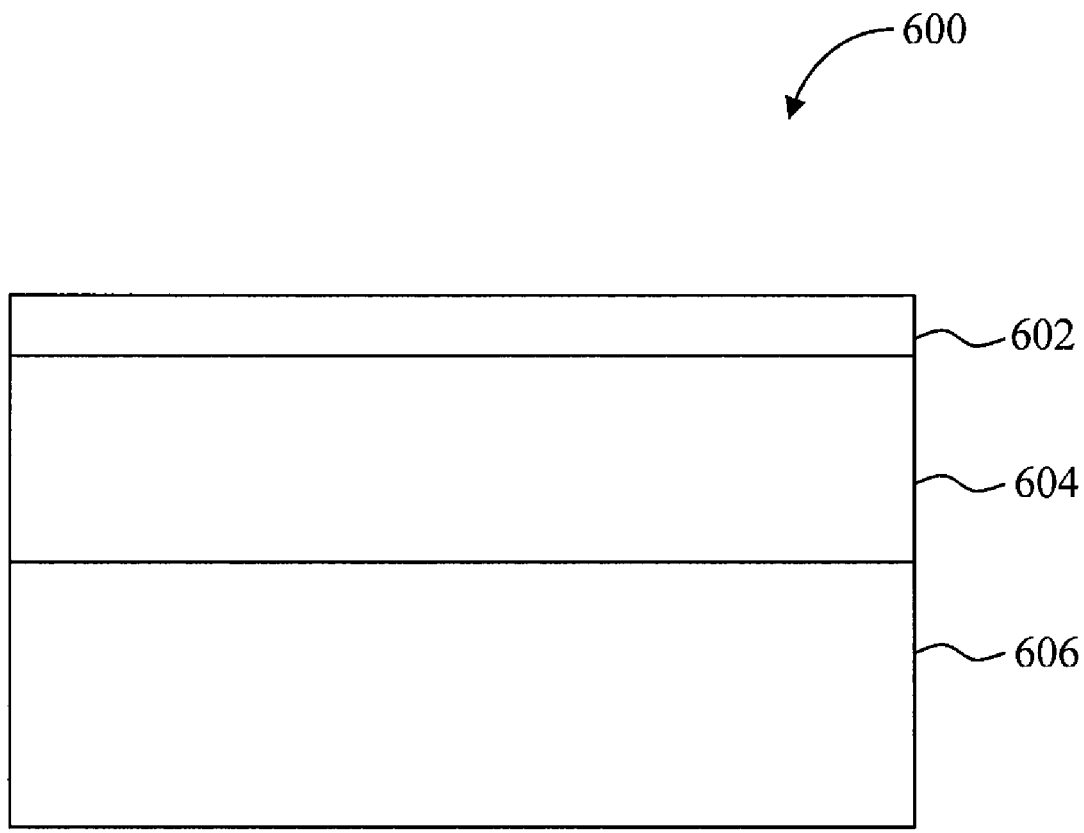
FIGS. 6-14 illustrate a method of forming a sensor in accordance with various embodiments of the invention.
Figure 7:
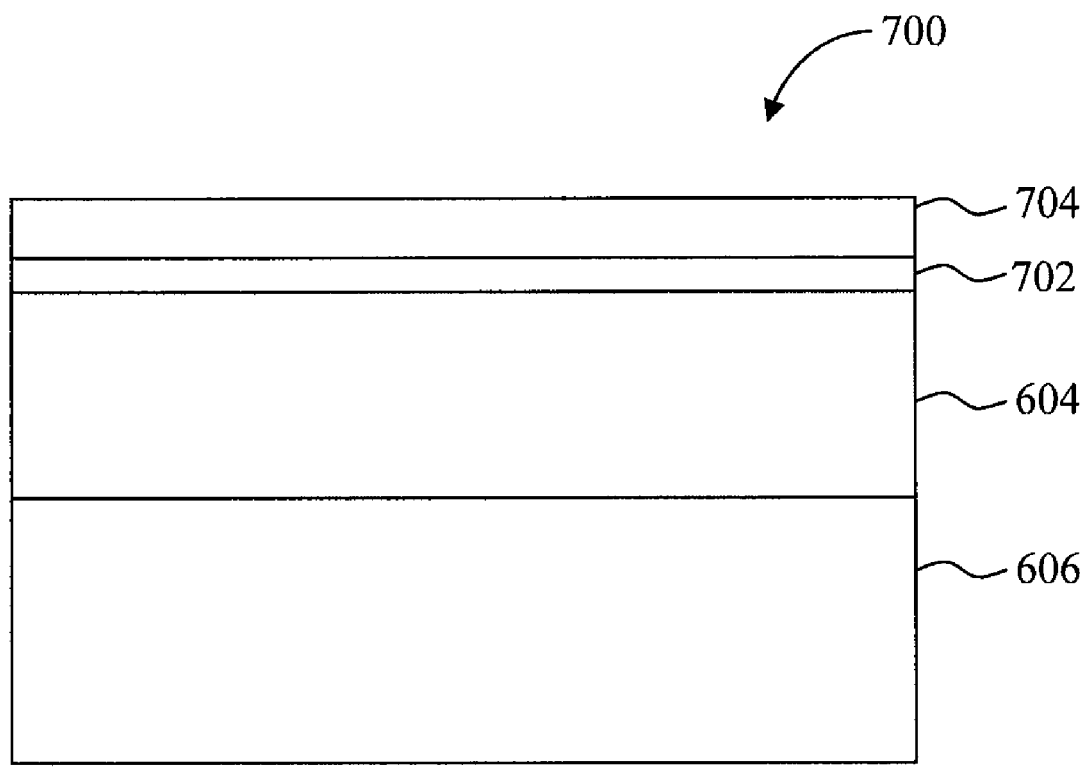
Figure 8:
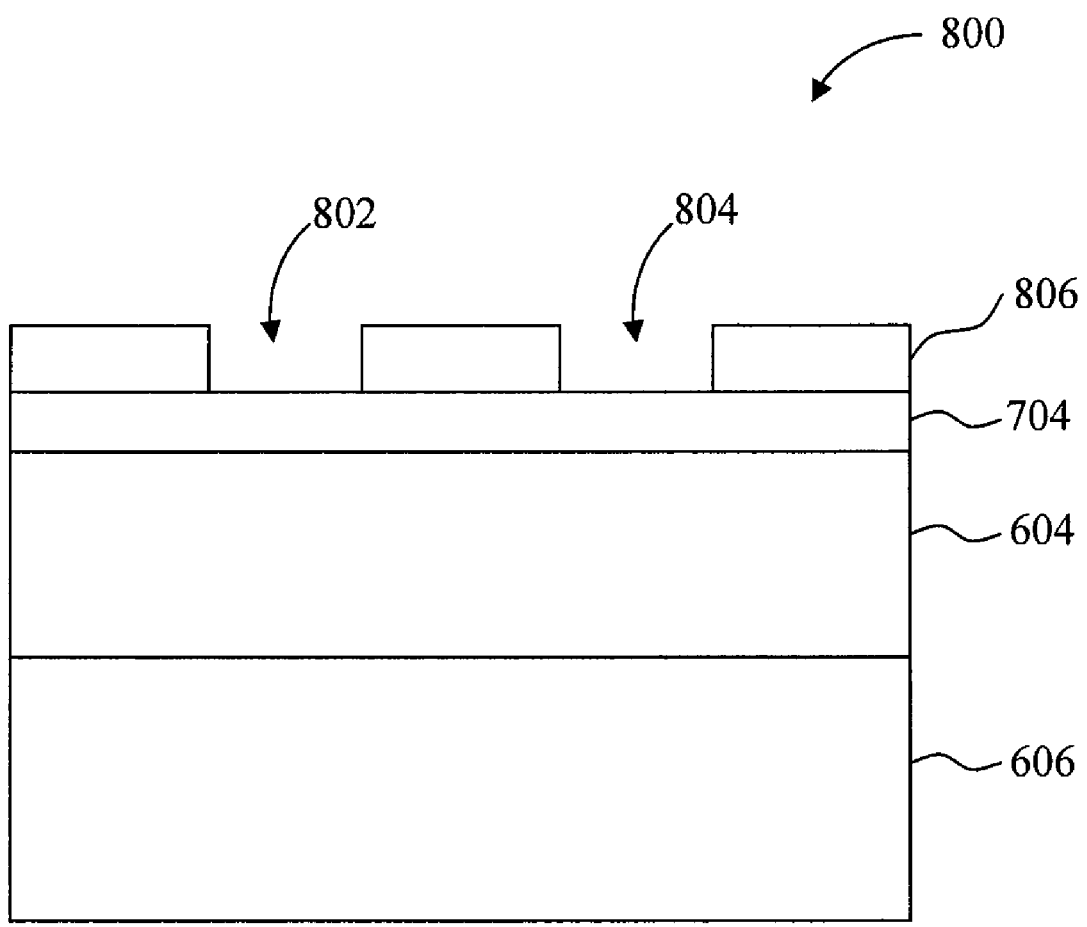
Figure 9:
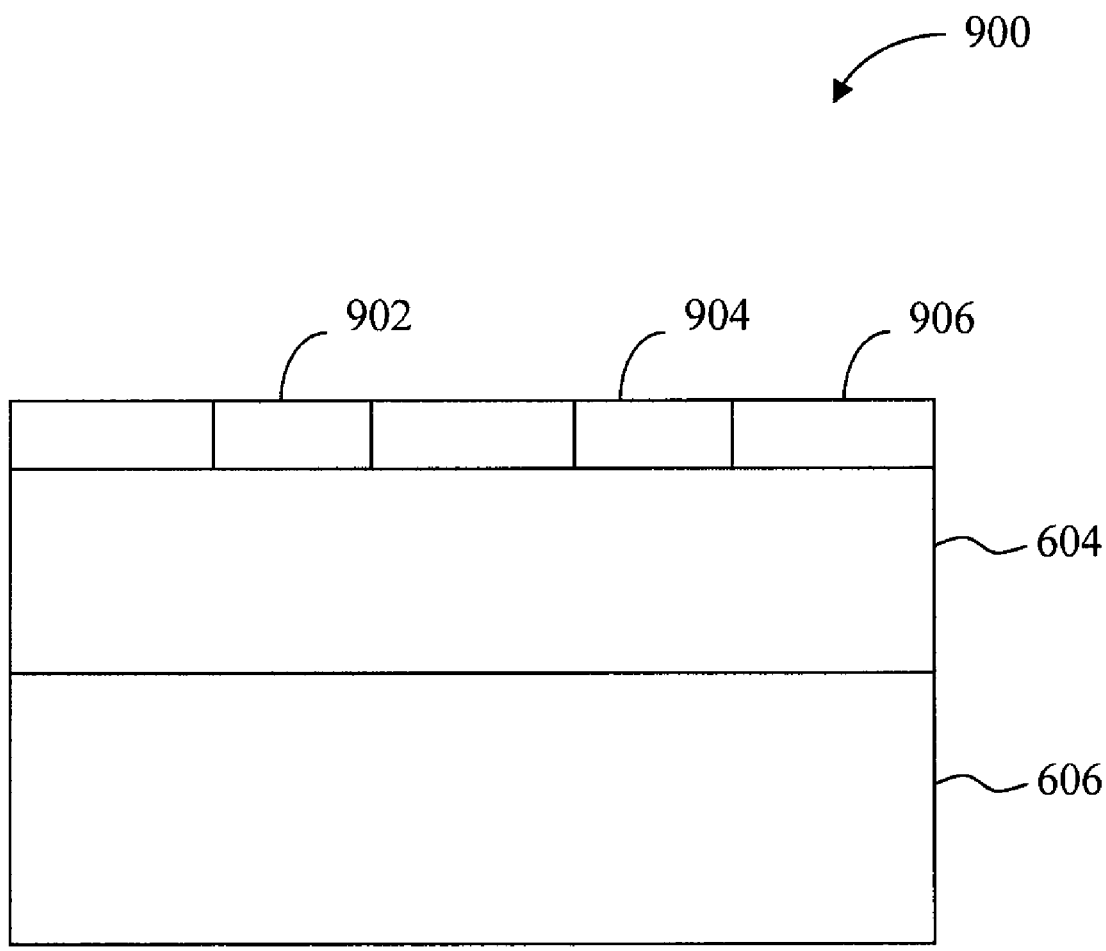

FIG. 6 illustrates a suitable starting material structure 600 for device 300 fabrication. Structure 600 is a p-type boron doped ($10^{15}$ $cm^3$) SOI wafer of resistivity ~20 Ohm-cm, produced using the separation by implanted oxygen SIMOX) process. An exemplary wafer can be obtained from IBIS technology Corporation. The initial thickness of a top silicon film layer 602 is greater than about 100 nm, with an underlying ion implanted buried oxide (BOX) layer 604 of thickness about 400 nm. Top silicon film 602 is thinned to about 100 nm using wet oxidation at about 1050° C. in a diffusion furnace for about 45 minutes, so that it is less than the Debye length of the minority carrier electrons (layer 702, illustrated in FIG. 7). Plasma enhanced chemical vapor deposition (PECVD) is performed to further increase the oxide thickness (layer 704). As discussed below, oxide layer 704 is also used as an effective mask for N+ phosphorous doping in subsequent processing. Next, positive photo resist OCG 825 is spin coated at about 4000 rpm for about 30 seconds to produce a photo resist layer, having a thickness of about 1000 Å. The resist is soft baked for about 15 minutes at about 80° C. A UV mask aligner is used to expose the resist for about 20 seconds through the n-well mask designed to open source drain windows for phosphorous doping. The exposed wafer is developed in OCG 945 developer for about 30 seconds, followed by a DI water rinse. The resist is then hard baked at about 115° C. for about 15 minutes. The hard baked resist protects the substrate during the buffered oxide etch (BOE) solution, which may be as long as about 30 minutes. Buffered oxide etch (BOE) is used to etch the top oxide for about 10 minutes to open the source drain doping windows 802, 804 in remaining oxide 806, as illustrated in FIG. 8. The photo resist is then stripped off using Microstrip 2000 stripper solution for about 20 minutes at about 100° C. Phosphorous doping of the exposed well regions on silicon is carried out in a solid source diffusion furnace at about 950° C. for about 30 minutes. Diffusion at about 950° C. for about 30 minutes gives an N+ junction depth on the order of one micron, with phosphorous doping density of ~$10^{19}$ cm$^{-3}$ and a resistivity of about 0.01 Ohm cm. Next, the masking oxide is removed by dipping the wafer in BOE for about 15 minutes, resulting in structure 900, illustrated in FIG. 9, having doped regions 902, 904, and silicon region 906.

Device isolation, in this process flow, is attained by physical separation of devices by plasma etching. On the other hand LOCOS or other suitable processes could alternatively be used for the device isolation.

Figure 10:
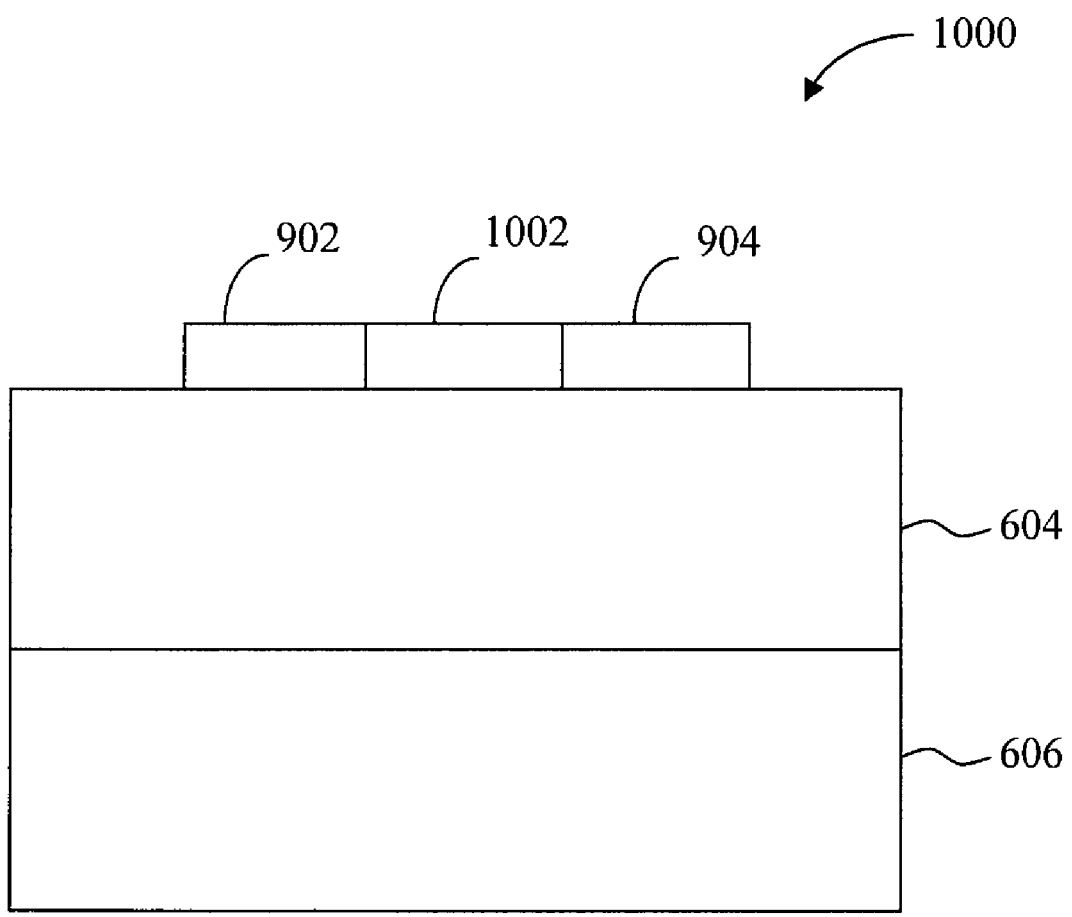

Turning now to FIG. 10, selective etching of silicon is carried out in a reactive ion etching (RIE) system using $SF_6$ etch chemistry. The wafer or substrate is spin coated with OCG825 photo resist and soft baked. The wafer is patterned with the active mask using the alignment marks as a guide, followed by photo resist development in OCG945 developer. The patterned photo resist is not hard baked for plasma etching of silicon. Silicon is selectively etched using $SF_6$ based gas chemistries—4 sccm of $SF_6$ gas flow at 20-millibar pressure, with 50 watt RF power applied for about 1 minute. The etch rate of silicon under these conditions is approximately 2000 Å per minute. The photo resist is then stripped off using Micro strip 2000 stripper solution. This results in structure 1000, which includes isolated silicon mesas 1002 on buried oxide 604, with source and drain regions 902, 904 on either side.

Figure 11:
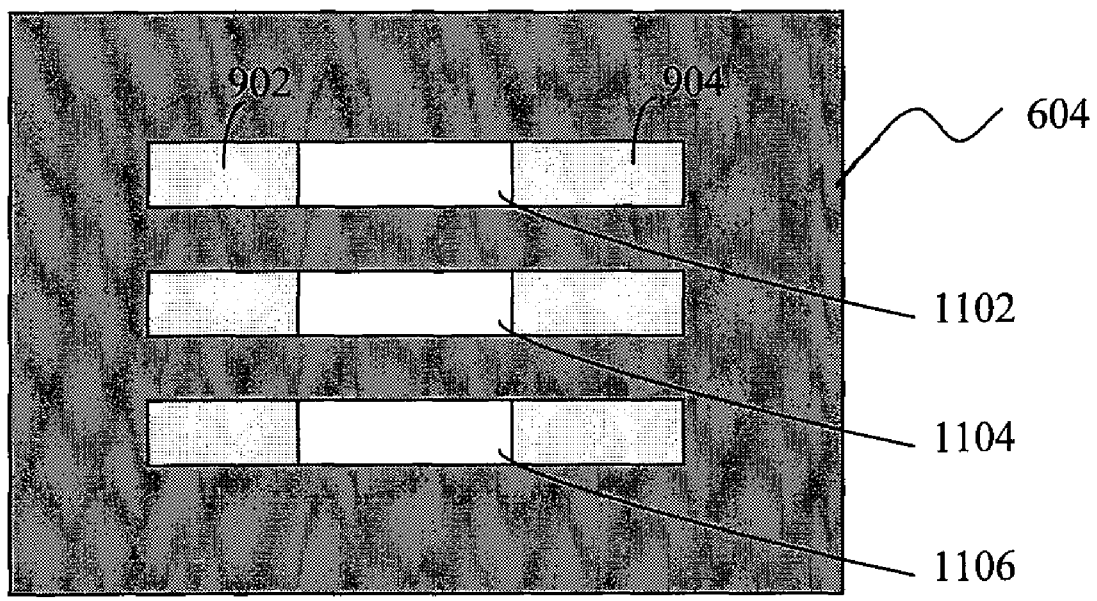
Figure 12:
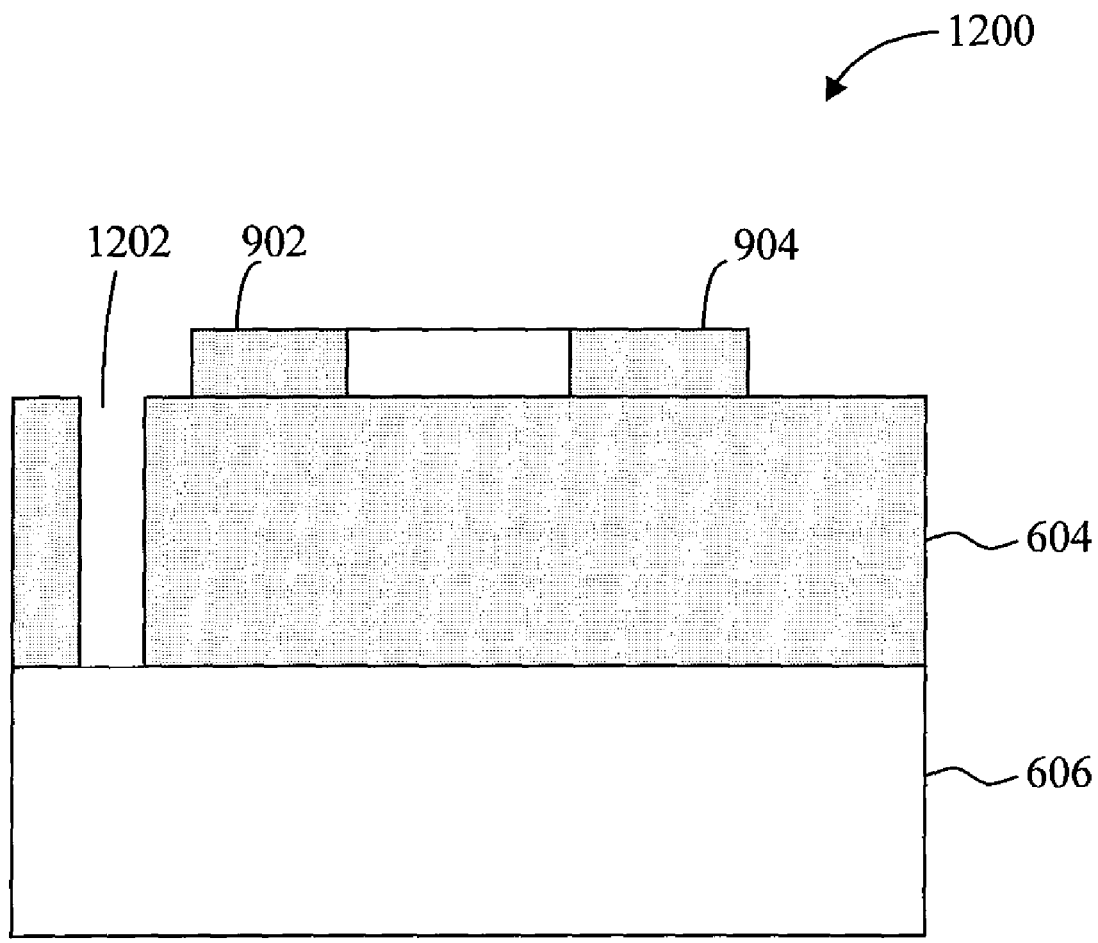
Figure 13:
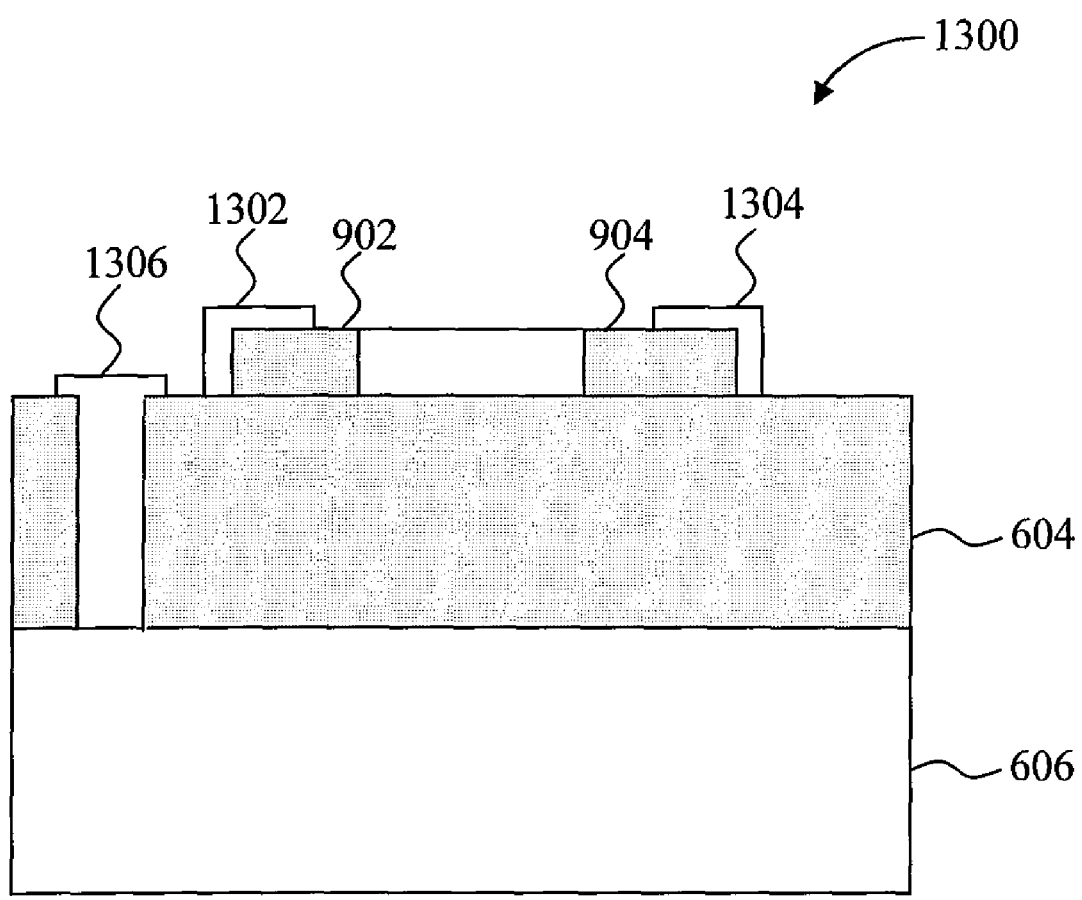

Silicon mesa 1002 surface is then coated with PMMA ebeam resist and patterned with E-beam lithography to obtain structure 1100, including nanowires 1102-1106 on the active area of the device surface, as illustrated in FIG. 11. Other known techniques for realizing nanowire or quantum wire structures such as template based selective etching or electrochemical etching or CVD deposition of silicon or molten state imprinting or laser etching or ion etching or particle etching or e-beam etching or chemically enhanced laser ablation can be alternatively used. The source—drain regions may be excluded from patterning. RIE etch of EBL patterned silicon yields nanowire devices of varying length to width ratios. In accordance with one embodiment of the invention, silicon channel 1002 is not etched all the way down to the buried oxide.

Contact to substrate 606 be formed using a well etch through buried oxide layer 604, to allow for electrical contact with the silicon substrate 606. This substrate contact enables ease in bonding and probing. To form the contact, the wafer is spin coated with OCG825 resist and patterned with optical aligner to open contact holes. The resist is developed and hard baked for about 15 minutes at about 115° C. The etch rate of buried oxide in BOE is approximately 600 Å per minute. The 4000 Å buried oxide is etched in BOE for 15 minutes, allowing for a slight over etch. The over etch is performed since the Si/$SiO_2$ interface is gradual and not sharp; in order to make a good electrical contact with the substrate, the structure is further etched in RIE using CF4 plasma for 1 minute. $CF_4$ etches both Si and $SiO_2$, hence enabling a good contact of metal with the silicon substrate. The RIE process recipe used is 50 sccm of CF4 at 50 millibar pressure with an applied RF power of 50 Watts. The photo resist is then stripped off in Microstrip 2000 solution, resulting in structure 1200, including a trench 1202.

To form the metal contacts, the wafer is spin coated with OCG825 resist and soft baked at 80° C. The wafer is patterned with the metal mask using optical aligner and developed. 2500 Å of gold is deposited on the exposed windows to make ohmic contacts 1302, 1304, with the source drain regions and contact 1306 to substrate 606. To get thicker gold metal layers AZ4330 resist is used. After deposition of gold, using either e-beam or thermal evaporation tools, lift off is carried out in acetone at 50° C. for half an hour. The device surface is then treated in buffered oxide etch (BOE) for 15 seconds, and fresh oxide of thickness 2 nm is grown on the silicon surface by immersing in hydrogen peroxide solution for thirty minutes. This can also be achieved by deposition of PECVD oxide or growth of wet oxide in particular conditions.

Figure 14:
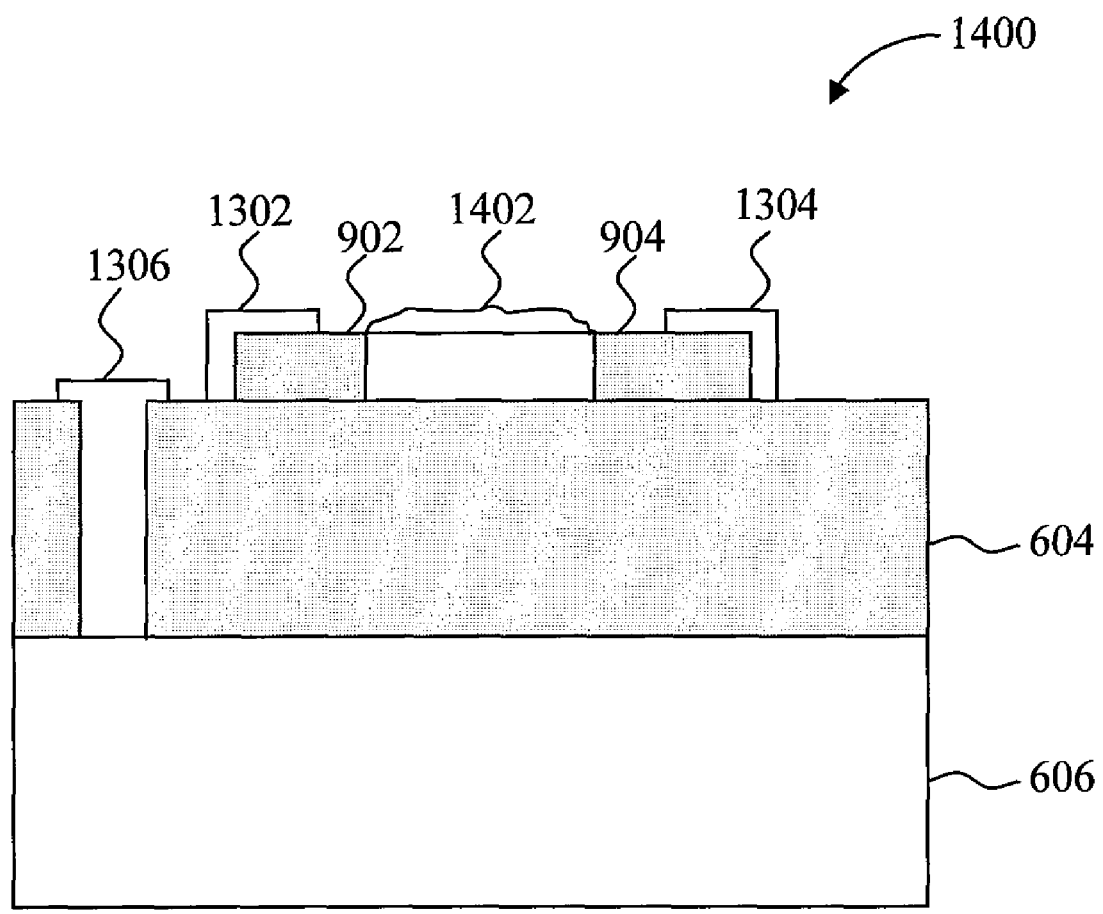

Finally, as illustrated in FIG. 14, the surface of the device is coated with the chemical sensitive layer 1402, which is predetermined to sense a specific target molecule, to form structure 1400. The surface coating of the chemical sensitive layer can be achieved by any of the process technologies. An example of this is coating of the device surface with metalloporphyrin monolayer (Langmuir Blodgett or by covalent attachment or contact imprint or similar technologies), which is sensitive to binding of amine molecules at the positively charged center metal atom.

Although the present invention is set forth herein in the context of the appended drawing figures, it should be appreciated that the invention is not limited to the specific form shown. For example, while the sensor device structures are conveniently described above in connection with a silicon substrate, the invention is not so limited; the structure of the present invention may additionally or alternatively be formed on alternative substrates. Furthermore, although only some of the devices are illustrated with particular layers, the devices and structures of the present invention may include additional layers, which are not illustrated. Various other modifications, variations, and enhancements in the design and arrangement of the method and apparatus set forth herein, may be made without departing from the spirit and scope of the present invention as set forth in the appended claims.

We claim:

1. A sensor for detecting a biological, chemical, or radioactive species, the sensor comprising:
   a substrate;
   an insulator formed overlying a portion of the substrate; and
   a quantum wire channel formed overlying the insulator, wherein the quantum wire is formed by patterning and removing a portion of the active region,
   wherein the sensor operates in a fully depleted mode, such that a sensed biological, chemical, or radioactive species causes an exponential change in channel conductance of the sensor.

2. The sensor for detecting a biological, chemical, or radioactive species wherein the substrate, the insulator, and the quantum wire channel are formed from a silicon-on-insulator substrate.

3. The sensor for detecting a biological, chemical, or radioactive species of claim 1, wherein a width of the quantum wire channel ranges from about 1 angstrom to about 1000 nm.

4. The sensor for detecting a biological, chemical, or radioactive species of claim 1, further comprising a dielectric material layer overlying the quantum wire channel.

5. The sensor for detecting a biological, chemical, or radioactive species of claim 4, wherein the dielectric material comprises material selected from the group consisting of $SiO_2$, $Si_3N_4$, SiNx, $Al2O_3$, AlOx $La2O_3$, $Y_2O_3$, $ZrO_2$, $Ta_2O_5$, $HfO_2$, $HfSiO_4$, HfOx, $TiO_2$, TiOx, a-$LaAlO_3$, $SrTiO_3$, $Ta_2O_5$, $ZrSiO_4$, BaO, CaO, MgO, SrO, $BaTiO_3$, $Sc_2O_3$, $Pr_2O_3$, $Gd_2O_3$, $Lu_2O_3$, TiN, $CeO_2$, BZT, BST, PVP-poly (4-vinyl phenol), PS-polystyrene, PMMA-polymethyl-methacrylate, PVA-polyvinyl alcohol, PVC-polyvinylchloride, PVDF-polyvinylidenfluoride, P$\alpha$MS-poly[$\alpha$-methylstyrene], CYEPL-cyano-ethylpullulan, BCB-divinyltetramethyldisiloxane-bis(benzocyclobutene), CPVP-Cn, CPS-Cn, PVP-CL, PVP-CP, polynorb, GR, nano $TiO_2$, OTS, Pho-OTS, and combinations thereof.

6. The sensor for detecting a biological, chemical, or radioactive species of claim 5, wherein the dielectric material is $SiO_2$.

7. The sensor for detecting a biological, chemical, or radioactive species of claim 1, further comprising a layer comprising a material selected from the group consisting of an antibody, a DNA hybridization sensor, a metallo porphyrin sensor, a mustard gas sensor, a molecular imprinted surface, and an ion sensor.

8. The sensor for detecting a biological, chemical, or radioactive species of claim 1, further comprising a dielectric layer overlying the quantum wire semiconductor channel and a material layer overlying the dielectric layer, wherein the material layer interacts with species from the group consisting of radioactive, chemical, and biological species.

9. The sensor for detecting a biological, chemical, or radioactive species of claim 1, when the quantum wire channel is an n-channel structure and addition of negative charge to a surface of the quantum wire channel causes an exponential increase of inversion channel conductance.

10. The sensor for detecting a biological, chemical, or radioactive species of claim 1, wherein the quantum wire channel is an n-channel structure and addition of a positive charge to the surface of the quantum wire channel causes an exponential decrease of the inversion channel conductance.

11. The sensor for detecting a biological, chemical, or radioactive species of claim 1, wherein the quantum wire channel is a p-channel structure and addition of a positive charge to a surface of the quantum wire channel causes an exponential increase of the inversion channel conductance.

12. The sensor for detecting a biological, chemical, or radioactive species of claim 1, wherein the quantum wire channel is a p-channel structure and addition of a negative charge to the surface of the quantum wire channel causes an exponential decrease of the inversion channel conductance.

13. A method of operating a sensor, the method comprising the steps of:
   providing a sensor comprising:
      a semiconductor substrate;
      an insulator formed overlying a portion of the substrate; and
      a quantum wire semiconductor channel formed overlying the insulator, wherein the quantum wire is formed by patterning and removing a portion of the active region,
   exposing the sensor to an atmosphere suspected of containing chemical, biological, or radioactive species;
   operating the sensor in a fully depleted mode; and
   measuring an exponential change in drain current upon detection of the chemical biological, or radioactive species.

14. A method of forming a solid-state sensor, the method comprising the steps of:
   providing a substrate;
   forming an insulator overlying the substrate; and
   forming a quantum wire channel region overlying the insulator, wherein the quantum wire is formed by patterning and removing a portion of the active region such that sensed species cause an exponential change in channel conductance.

15. The method of claim 14, further comprising the step of forming a chemical, biological, or radioactive sensitive material overlying the channel region.

16. The method of claim 14, further comprising the step of forming a dielectric layer overlying the channel region.

17. The method of claim 16, further comprising the step of forming a chemical, biological, or radioactive sensitive material overlying the dielectric layer.

18. A sensor for detecting a biological, chemical, or radioactive species, the sensor comprising:
   an insulator; and
   a quantum wire channel formed overlying the insulator, wherein the quantum wire is formed by patterning and removing a portion of the active region,
   wherein the sensor operates in a fully depleted mode, such that a sensed biological, chemical, or radioactive species causes an exponential change in channel conductance of the sensor, and wherein the channel is fully depleted without any need for a gate bias.

19. The sensor for detecting a biological, chemical, or radioactive species of claim 18, further comprising a dielectric material layer overlying the quantum wire channel.

20. The sensor for detecting a biological, chemical, or radioactive species of claim 18, further comprising a dielectric layer overlying the quantum wire semiconductor channel and a material layer overlying the dielectric layer, wherein the material layer interacts with species from the group consisting of radioactive, chemical, and biological species.

* * * * *